CHRYSANTHEMUM PLANT
Filed Dec. 17, 1975
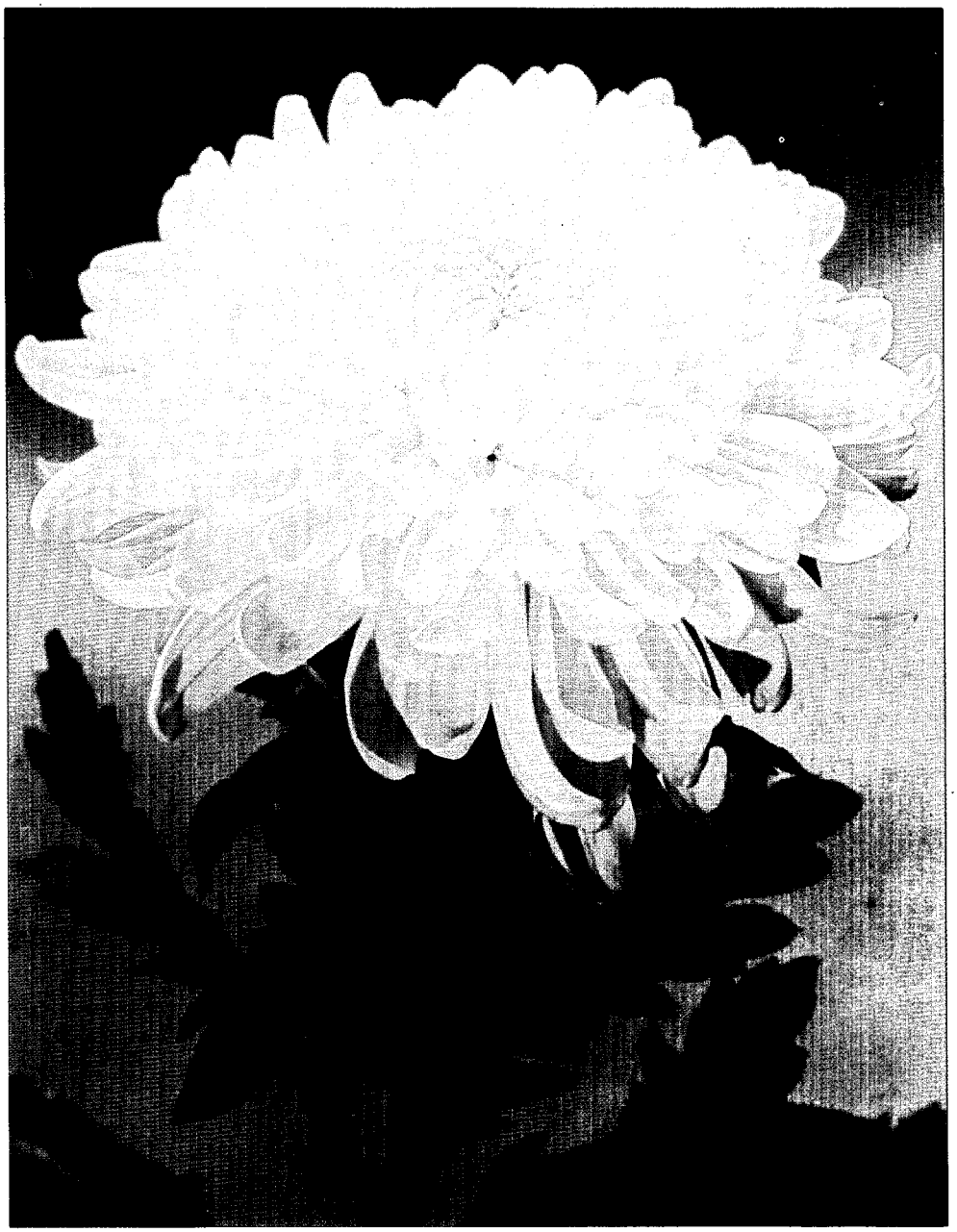

United States Patent

Plant Pat. 3,986
Patented Nov. 30, 1976

3,986

CHRYSANTHEMUM PLANT

Walter H. Jessel, Jr., Doylestown, and William E. Duffett, Akron, Ohio, assignors to Yoder Brothers, Inc., Barberton, Ohio Filed Dec. 17, 1975, Ser. No. 641,773
Int. Cl.[2] A01H 5/00
U.S. Cl. Plt.—78 1 Claim The present invention comprises a new and distinct cultivar of *Chrysanthemum morifolium*, Ramat., hereinafter referred to by the cultivar name Yellow Palisade (#70269A12).

Yellow Palisade is a product of a planned sport induction program which had the objective of expanding the color range of the parental cultivar, Palisade. Palisade was a product of a planned breeding program which had the objective of creating new cultivars with standard type inflorens, uniform nine-week response, large inflorescence size, excellent shipping durability, and the ability to produce commercially acceptable quality during high light and high temperature periods.

Yellow Palisade is an induced sport of Palisade (#70269012), disclosed in our pending U.S. application Ser. No. 608,257, filed Aug. 27, 1975. Yellow Palisade was discovered and selected by William E. Duffett and Walter H. Jessel, Jr. on Dec. 11, 1974 as one plant within a flowering block of Palisade in a controlled environment in Barberton, Ohio. Plants within the flowering block were derived from stock plants which had been irradiated as rooted cuttings with an X-ray source of 1800 r units.

Palisade, the parental cultivar of Yellow Palisade, was originated by the present inventors in 1969 as a product of a controlled breeding program. The female, or seed parent, was Snowdon (#21660E01; unpatented; commercially available), a white standard of parentage unknown to the present inventors. The male, or pollen parent of Palisade, was #67016999 (unnamed seedling), a white standard originated by the present inventors.

The first act of asexual reproduction of Yellow Palisade was accomplished when vegetative cuttings were taken from the initial selection in February 1975 in a controlled environment in Barberton, Ohio by a technician working under formulations established and supervised by William E. Duffet and Water H. Jessel, Jr. Horticultural examination of selected units initiated Dec. 13, 1974 has demonstrated that the combination of characteristics as herein disclosed for Yellow Palisade are firmly fixed and are retained through successive generations of asexual reproduction.

Yellow Palisade has not been observed under all possible environmental conditions. The phenotype may vary significantly with variations in environment such as temperature, light intensity, and daylength. The following observations, measurements, and comparisons describe plants grown in Barberton, Ohio under greenhouse environmental conditions which approximate those generally used in commercial practice, as described in Chart A and Chart B which appears at the end of the present specification. A light intensity chart of general use is shown in FIG. 14.14 in ASHAE Trans., vol. 64, page 64, and reference is made thereto.

The following traits have been repeatedly observed and are determined to be basic charcateristics of Yellow Palisade which in combination distinguish this chrysanthemum as a new and distinct cultivar:

(1) Standard (disbud) to decorative (spray) inflorescence type.

(2) Semi-incurve (disbud) to flat (spray) inflorescence form.

(3) Yellow inflorescence color.

(4) Diameter across face of inflorescence from 3.5 to 4.5 inches (spray) and from 5.0 to 6.5 inches (disbud) at maturity.

(5) Uniform nine-week (disbud) and ten-week (spray) flowering response.

(6) Tall plant height.

(7) Upright branching pattern.

(8) Good shipping durability.

(9) High grade-out (Society of American Florists Standards).

The accompanying photographic drawing depicts the distinguishing feature of yellow inflorescence color of Yellow Paliside. Color representations are as nearly true as possible with illustrations of this type.

Of the many commercial cultivars known to the present inventors, the most similar existing cultivar in comparison to Yellow Palisade is the parental cultivar, Palisade. Reference is made to attach Chart B which compares certain characteristics of Palisade with the same characteristics of Yellow Palisade. In comparison to Palisade, Yellow Palisade has different inflorescence color. The diameter across face of inflorescence, plant height, branching pattern, flowering response period, inflorescence form, and inflorescence type of Yellow Palisade are similar to those of Palisade.

In the following description, color references are made to The Munsell Limit Color Cascade, 1972 edition. The color values were determined between 2:30 and 3:00 p.m. on Aug. 1, 1975 under 150 foot-candle light intensity at Barberton, Ohio.

Botanical classification: *Chrysanthemum morifolium*, Ramat., cv Yellow Palisade.

I. INFLORESCENCE

A. Capitulum:
- *Form.*—Semi-incurved (disbud) to flat (spray).
- *Type.*—Standard (disbud) to decorative (spray).
- *Permanence.*—14–18 days.
- *Diameter across face.*—3.5 to 4.5 inches (spray) and 5.0 to 6.5 inches (disbud).

B. Corolla of ray florets:
- *Texture (adaxial).*—Glabrous.
- *Appearance and form.*—Ligulate.
- *Arrangement.*—Whorled on receptacle.
- *Persistence.*—Resists shatter.
- *Color (abaxial).*—26–1 to 26–5.
- *Color (adaxial).*—26–1 to 26–5.

C. Reproductive organs:
- *Androecium.*—Present disc florets only; syngenesious stamen: scant pollen.
- *Gynoecium.*—Present both ray and disc florets; inferior, bicarpellate ovary; single style; 2-lobed stigma.

II. PLANT

A. General appearance: Upright; tall height.

B. Duration and texture: Perennial; herbaceous.

C. Foliage:
- *Color (abaxial).*—20–15 to 20–12.
- *Color (adaxial).*—20–11, but not more greyed.
- *Shape.*—Spatulate; deeply lobed.
- *Texture.*—Glabrous.
- *Arrangement.*—Alternate.
- *Venation.*—Prominent.
- *Margin.*—Moderately serrated.

CHART A—AVERAGE GREENHOUSE CHRYSANTHEMUM ENVIRONMENTS USED FOR BARBERTON, OHIO

| Season | Temperatures used (° F.) | | | Lighting used | Black cloth used | Supp., $CO_2$ |
|---|---|---|---|---|---|---|
| | Night | Bright day | Cloudy day | | | |
| Fall | 65 to 56 | 65 to 80 | 60 to 75 | 2 to 4 weeks at 3 hours per night of 7–10 f.c. | To Sept. 15: on, 5:30 p.m.; off, 7:30 a.m. | From Oct. 15: 300 p.p.m. |
| Winter | 58 to 62 | 65 to 70 | 60 to 65 | 2 to 5 weeks at 5 hours per night of 7–10 f.c. | None | 300 p.p.m. |
| Spring | 58 to 65 | 65 to 80 | 60 to 75 | 2 to 4 weeks at 5 hours per night of 7–10 f.c. | From Mar. 15: on, 5:30 p.m.; off, 7:30 a.m. | To Apr. 15: 300 p.p.m. |
| Summer | 62 to 68 | 70 to 90 | 65 to 75 | 1 to 2 weeks at 3 hours per night of 7–10 f.c. | On, 6:00 p.m.; off, 8:00 a.m. | None. |

CHART B—COMPARISON OF YELLOW PALISADE AND PALISADE

| Cultivar | Inflorescence color | Diameter across face of inflorescence | Plant height | Branching pattern | Flowering response period | Inflorescence form and type |
|---|---|---|---|---|---|---|
| Yellow Palisade | Yellow | 3.5 to 4.5 inches (spray) and 5.0 to 6.5 inches (disbud). | Tall | Upright | 9 week (disbud) to to 10 week (spray). | Semi-incurved standard (disbud) flat decorative (spray). |
| Palisade | White | do | do | Upright | do | Do. |

Comparisons made of plants grown in a greenhouse in Barberton, Ohio under environmental conditions as described in Chart A.

We claim:

1. A new and distinct cultivar of chrysanthemum plant known by the cultivar name Yellow Palisade and particularly characterized as to uniqueness by the combined characteristics of standard (disbud) to decorative (spray) inflorescence type; semi-incurve (disbud) to flat (spray) inflorescence form; yellow inflorescence color; diameter across face of inflorescence from 3.5 to 4.5 inches (spray) and from 5.0 to 6.5 inches (disbud) at maturity; uniform nine-week (disbud) and ten-week (spray) flowering response; tall plant height; upright branching pattern; good shipping durability, and high grade-out (Society of American Florists Standards).

No references cited.

ROBERT E. BAGWILL, Primary Examiner